United States Patent
Emerson et al.

(10) Patent No.: US 8,914,107 B2
(45) Date of Patent: Dec. 16, 2014

(54) VENTILATION SENSOR RATE RESPONSE NORMALIZATION AND CALCULATION

(75) Inventors: Paul F. Emerson, St. Louis Park, MN (US); Gary T. Seim, Minneapolis, MN (US); Michael A. Querimit, Fridley, MN (US); Donald L. Hopper, Maple Grove, MN (US); Stephen R. Pitzl, Shoreview, MN (US); Daniel O'Brien, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 654 days.

(21) Appl. No.: 12/784,151

(22) Filed: May 20, 2010

(65) Prior Publication Data

US 2010/0305643 A1 Dec. 2, 2010

Related U.S. Application Data

(60) Provisional application No. 61/181,044, filed on May 26, 2009.

(51) Int. Cl.
*A61N 1/365* (2006.01)
*A61N 1/362* (2006.01)
*A61N 1/37* (2006.01)

(52) U.S. Cl.
CPC ............ *A61N 1/36521* (2013.01); *A61N 1/362* (2013.01); *A61N 1/37* (2013.01); *A61N 1/365* (2013.01)
USPC ........ 607/17; 607/9; 607/11; 607/18; 607/19; 607/20; 607/115; 607/119; 600/508; 600/509; 600/510; 600/513; 600/532; 600/538; 600/543

(58) Field of Classification Search
CPC ....... A61N 1/365; A61N 1/3601; A61N 1/37; A61N 1/36514; A61N 1/362; A61N 1/36; A61N 1/3611; A61N 1/36135; A61N 1/37282; A61N 1/3702; A61B 5/0205; A61B 5/0816; A61B 5/087; A61B 5/0803; A61B 5/091; A61B 5/0002; A61B 5/0022; G06Q 50/22; G06F 19/322; G06F 19/3437; Y10S 128/92
USPC ......... 600/481, 483–484, 508–510, 513, 532, 600/538, 543; 607/1–2, 9, 11, 17–20, 115, 607/119
See application file for complete search history.

(56) References Cited

U.S. PATENT DOCUMENTS 5,156,147 A 10/1992 Warren et al.
5,235,976 A 8/1993 Spinelli
(Continued)

FOREIGN PATENT DOCUMENTS

EP 0327292 A1 8/1989
EP 0804940 A2 11/1997
(Continued)

OTHER PUBLICATIONS

"European Application Serial No. 10720500.7, Response filed Aug. 6, 2012 to Office Action mailed Feb. 3, 2012", 11 pgs.
(Continued)

*Primary Examiner* — Deborah Malamud
(74) *Attorney, Agent, or Firm* — Schwegman Lundberg & Woessner, P.A.

(57) ABSTRACT

A cardiac rhythm management (CRM) device can extract ventilation information from thoracic impedance or other information, and adjust a delivery rate of the CRM therapy. A tidal volume of a patient is measured and used to adjust a ventilation rate response factor. The measured tidal volume can optionally be adjusted using a ventilation rate dependent adjustment factor. The ventilation rate response factor can also be adjusted using a maximum voluntary ventilation (MVV), an age predicted maximum heart rate, a resting heart rate, and a resting ventilation determined for the patient. In various examples, a global ventilation sensor rate response factor (for a population) can be programmed into the CRM device, and automatically tailored to be appropriate for a particular patient.

8 Claims, 5 Drawing Sheets

(56) References Cited

U.S. PATENT DOCUMENTS

| | | | |
|---|---|---|---|
| 5,284,136 | A | 2/1994 | Hauck et al. |
| 5,318,597 | A | 6/1994 | Hauck et al. |
| 5,487,753 | A | 1/1996 | MacCarter et al. |
| 6,076,015 | A | 6/2000 | Hartley et al. |
| 6,161,042 | A | 12/2000 | Hartley et al. |
| 6,463,326 | B1 | 10/2002 | Hartley et al. |
| 7,567,839 | B2 * | 7/2009 | Sun et al. .................. 607/19 |
| 2003/0105499 | A1 | 6/2003 | Hartley et al. |
| 2006/0247704 | A1 | 11/2006 | Sun et al. |

FOREIGN PATENT DOCUMENTS

| | | |
|---|---|---|
| EP | 2435133 B1 | 4/2014 |
| JP | 2012527960 A | 11/2012 |
| WO | WO-99/43385 A1 | 9/1999 |
| WO | WO-2010/138388 A1 | 12/2010 |

OTHER PUBLICATIONS

"International Application Serial No. PCT/US2010/035608, International Preliminary Report on Patentability mailed Dec. 8, 2011", 10 pgs.

"Japanese Application Serial No. 2012-513139, Office Action mailed May 22, 2012", (w/ English Translation), 6 pgs.

"Japanese Application Serial No. 2012-513139, Response filed Aug. 22, 2012 to Office Action mailed May 22, 2012", (w/ English Translation of Amended Claims), 8 pgs.

Blackie, S. P, et al., "Normal values and ranges for ventilation and breathing pattern at maximal exercise.", *Chest*, 100(1), (Jul. 1991), 136-42.

Clark, T. J, et al., "The ventilatory capacity of patients with chronic airways obstruction.", *Clin Sci.*, 36(2), (Apr. 1969), 307-16.

Lorusso, T. J, et al., "Prediction of maximal exercise capacity in obstructive and restrictive pulmonary disease.", *Chest*, 104(6), (Dec. 1993), 1748-54.

Mahler, D. A, et al., "Exercise performance in marathon runners with airway obstruction.", *Med Sci Sports Exerc.*, 13(5), (1981), 284-9.

Medoff, B. D, et al., "Breathing reserve at the lactate threshold to differentiate a pulmonary mechanical from cardiovascular limit to exercise.", *Chest*, 113(4), (Apr. 1998), 913-8.

"International Application Serial No. PCT/US2010/035608, International Search Report mailed Jul. 26, 2010", 5 pgs.

"International Application Serial No. PCT/US2010/035608, Written Opinion mailed Jul. 26, 2010", 8 Pgs.

* cited by examiner

VENTILATION SENSOR RATE RESPONSE NORMALIZATION AND CALCULATION

CLAIM OF PRIORITY

This patent application claims the benefit of priority, under 35 U.S.C. Section 119(e), to Paul Emerson et al., U.S. Provisional Patent Application Ser. No. 61/181,044, entitled "Ventilation Sensor Rate Response Normalization and Calculation," filed on May 26, 2009, which is hereby incorporated by reference in its entirety.

BACKGROUND

Implantable medical devices (IMDs) include devices designed to be implanted into a patient. Some examples of these devices are cardiac function management (CFM) devices such as implantable pacemakers, implantable cardioverter defibrillators (ICDs), cardiac resynchronization therapy devices (CRTs), neuromodulation devices, or devices that include a combination of such capabilities. Such devices can often be used to treat patients using electrical or other therapy or to aid a physician or caregiver in patient diagnosis through internal monitoring of a patient's condition. The devices can include one or more electrodes in communication with one or more sense amplifiers to monitor electrical heart activity within a patient, and often include one or more physiological sensors to monitor one or more other internal patient parameters. Other examples of implantable medical devices include implantable diagnostic devices, implantable drug delivery systems, or implantable devices with neural stimulation capability, some of which can also be used as CFM devices.

OVERVIEW

This document relates generally to systems, devices, and methods for normalizing and calculating a minute ventilation rate response factor for a minute ventilation or other ventilation sensor.

Minute Ventilation (also referred to as "minute volume" or "MV") is a respiratory-related parameter that is a measure of the volume of air inhaled and exhaled during a one-minute time interval. Minute ventilation can be conceptualized as the product of a patient's ventilation rate and the patient's tidal volume of air inhaled and exhaled during a particular breath. One or both of the patient's ventilation rate or tidal volume can be sensed using an impedance sensor that measures transthoracic impedance, which is modulated by the patient's breathing. Minute ventilation correlates well with the patient's metabolic need for an increased heart rate over a range of heart rates.

Typically, patients have similar potential heart rate range depending on their age. However, ohmic tidal volume measured in patients can differ substantially based on their chest size, the positioning of impedance sensors within the body cavity, current paths taken within the body cavity, etc. Large individuals with large thoracic movements may exhibit greater impedance differences than smaller individuals with smaller impedance differences. However, both types of individuals may have the same heart rate range. Additionally, deep breaths detected by a thoracic impedance sensor at a lower gain setting could have the same digitized tidal volume output as shallow breaths at a higher gain setting. Variation in tidal volume measurement can lead to inaccurate measurement of minute ventilation, which, in turn, can affect pacing therapy that can be based at least in part on the minute ventilation.

Example 1 includes a cardiac rhythm management system. In this example, the system optionally includes a signal processor configured to measure a tidal volume of a patient and to adjust a ventilation sensor rate response factor using information determined from the measured tidal volume. In this example, the system optionally includes a controller coupled to the signal processor, the controller configured to calculate a ventilation sensor driven pacing rate, including applying the adjusted ventilation sensor rate response factor to a deviation in an observed ventilation sensor output from a baseline.

In Example 2, the subject matter of Example 1 optionally includes a signal processor configured to adjust the ventilation sensor rate response using information obtained from a patient population.

In Example 3, the subject matter of any one or more of Examples 1-2 optionally includes a signal processor configured to adjust the ventilation sensor rate response factor using a ventilation rate dependent adjustment factor to generate an adjusted tidal volume.

In Example 4, the subject matter of any one or more of Examples 1-3 optionally includes a ventilation rate dependent adjustment factor configured to compensate for a filter non-ideality in the signal processor.

In Example 5, the subject matter of any one or more of Examples 1-4 optionally includes a signal processor including or coupled to a memory configured to store a plurality of resting tidal volumes, the signal processor comprising a central tendency computation circuit configured to compute a central tendency of the plurality of resting tidal volumes.

In Example 6, the subject matter of any one or more of Examples 1-5 optionally includes a signal processor configured to adjust the ventilation sensor rate response factor using information determined from the measured tidal volume, including using the measured tidal volume to determine a normalization factor using a population-determined relationship between the tidal volume and the normalization factor.

In Example 7, the subject matter of any one or more of Examples 1-6 optionally includes a population-determined relationship between the tidal volume and the normalization factor comprising a substantially inverse linear relationship for the normalization factor as a function of the tidal volume.

In Example 8, the subject matter of any one or more of Examples 1-7 optionally includes a population-determined relationship between the tidal volume and the normalization factor comprising about a 4-to-1 range of the normalization factor over an expected range of tidal volumes for the population.

In Example 9, the subject matter of any one or more of Examples 1-8 optionally includes a signal processor configured to adjust a ventilation sensor rate response factor using information determined from the measured tidal volume, including using a population-based ventilation rate response factor programmed into a cardiac rhythm management device, and automatically adjusting the population based ventilation rate response factor for the patient using a normalization factor determined using the measured tidal volume of the patient.

In Example 10, the subject matter of any one or more of Examples 1-9 optionally includes a signal processor configured to adjust a ventilation sensor rate response factor using a measured minute ventilation at rest, an exercise equivalent minute ventilation, a resting heart rate, and an age predicted maximum heart rate determined for the patient.

The subject matter of Example 11 can include a process, or a memory circuit coupled to a processor, the memory circuit including instructions causing the processor to control or perform one or more of measuring a tidal volume of a patient, adjusting a ventilation sensor rate response factor using information determined from the measured tidal volume, and calculating a ventilation sensor driven pacing rate, including applying the adjusted ventilation sensor rate response factor to a deviation in an observed ventilation sensor output from a baseline.

In Example 12, the subject matter of any one or more of Examples 1-11 optionally includes adjusting the ventilation sensor rate response using information obtained from a patient population.

In Example 13, the subject matter of any one or more of Examples 1-12 optionally includes adjusting the ventilation rate response factor using a measured minute ventilation at rest, an exercise equivalent minute ventilation, a resting heart rate, and an age predicted maximum heart rate determined for the patient.

In Example 14, the subject matter of any one or more of Examples 1-13 optionally includes scaling the maximum voluntary ventilation using a scaling factor, the scaling factor selected based on the patient's physical health condition.

In Example 15, the subject matter of any one or more of Examples 1-14 optionally includes adjusting the measured tidal volume using a ventilation rate dependent adjustment to generate an adjusted measured tidal volume.

In Example 16, the subject matter of any one or more of Examples 1-15 optionally includes measuring the tidal volume including receiving a plurality of resting tidal volumes, and computing a central tendency of a plurality of measured tidal volumes.

In Example 17, the subject matter of any one or more of Examples 1-16 optionally includes measuring the tidal volume and computing the central tendency of a plurality of the adjusted measured tidal volumes using an implantable medical device.

In Example 18, the subject matter of any one or more of Examples 1-17 optionally includes adjusting the ventilation sensor rate response factor using information determined from the measured tidal volume using the measured tidal volume to determine a normalization factor using a population-determined relationship between the tidal volume and the normalization factor.

In Example 19, the subject matter of any one or more of Examples 1-18 optionally includes using a population-determined relationship between the tidal volume and the normalization factor including a substantially inverse linear relationship for the normalization factor as a function of the tidal volume.

In Example 20, the subject matter of any one or more of Examples 1-19 optionally includes using a tidal volume measured during a maximum voluntary ventilation period.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This document relates generally to systems, devices, and methods for normalizing a minute ventilation rate response factor for a minute ventilation or other ventilation sensor.

Figure 1:
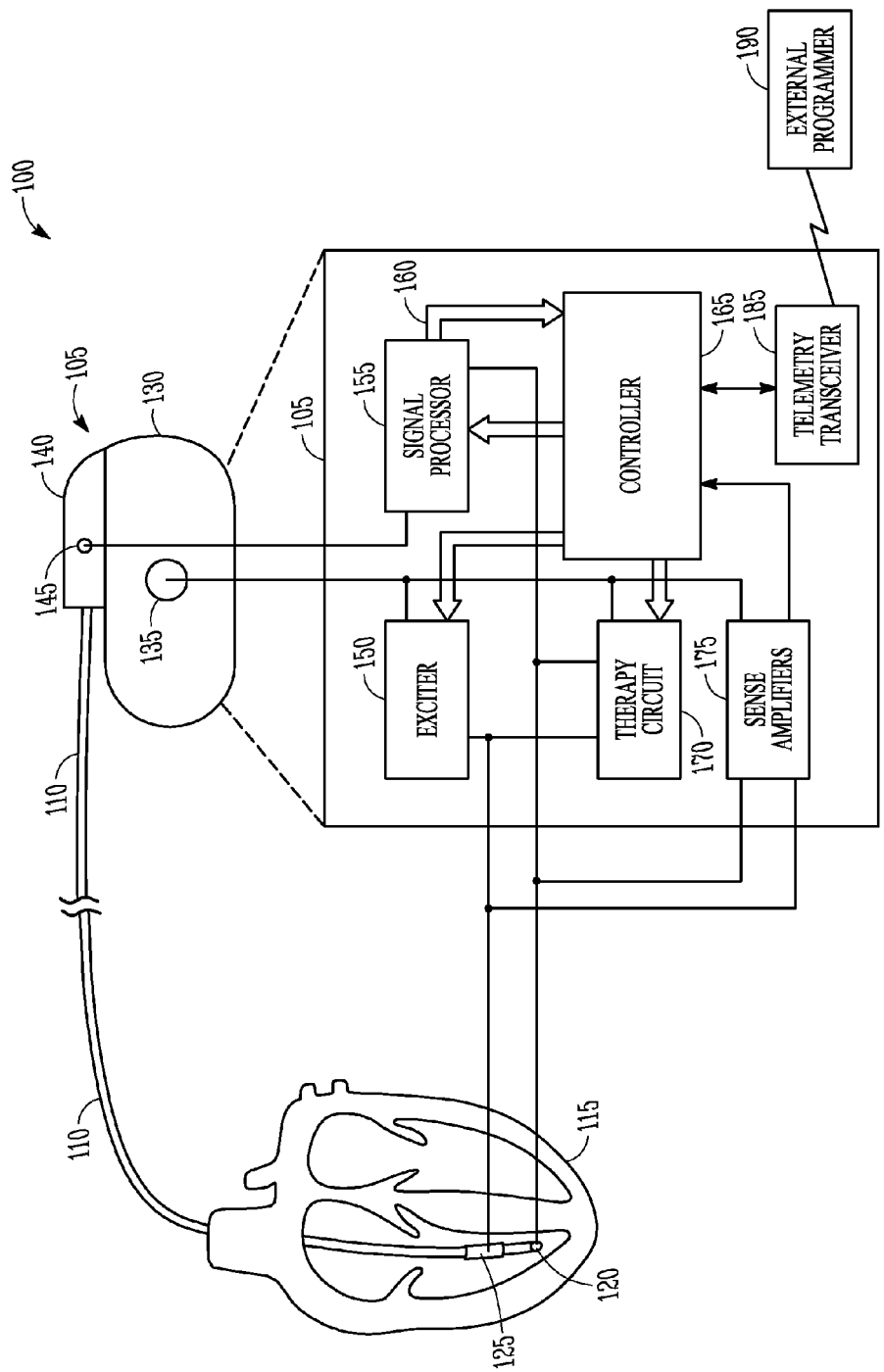
FIG. 1 is an illustration of an example of an implantable medical device including a cardiac rhythm management device and electrode connections.

FIG. 1 illustrates an example of a cardiac rhythm management system 100. In this example, the system 100 can include, among other things, a cardiac rhythm management device 105 and a leadwire ("lead") 110 for communicating signals between the device 105 and a portion of a living organism, such as a heart 115. Examples of the device 105 can include bradycardia and antitachycardia pacemakers, cardioverters, defibrillators, combination pacemaker/defibrillators, neuromodulation devices, drug delivery devices, and any other cardiac rhythm management apparatus capable of monitoring cardiovascular function or providing cardiovascular therapy such as for benefit of the heart 115. The system 100 can also include additional components such as, for example, a local or remote programmer capable of communicating with the device 105.

In an example, the system 100 can be implantable in a living organism, such as in a pectoral or abdominal region of a human patient, or elsewhere. In an example, one or more portions of the system 100 (e.g., device 105) can be disposed external to the human patient. In the illustrated example, portions of the lead 110 are disposed in the right ventricle; however, any other positioning of lead 110 can be used. For example, the lead 110 can be positioned in the atrium or elsewhere. In an example, the lead 110 can be a commercially available bipolar pacing lead. The system 100 can also include one or more other leads or electrodes (e.g., with a lead, or leadless), such as in addition to lead 110, appropriately disposed, such as in or around heart 115, or elsewhere.

In an example, the system 100 can include at least four electrodes, such as described in Hauck et al. U.S. Pat. No. 5,284,136 entitled "DUAL INDIFFERENT ELECTRODE PACEMAKER," assigned to the assignee of the present patent application, the disclosure of which is incorporated herein by reference in its entirety, including its description of an impedance sensing system. The present systems and methods can also include using a different number of electrodes (e.g., 2 or 3 electrodes, or more than 4 electrodes). In an example, a first conductor of the multiconductor lead 110 can electrically couple a first electrode, such as a tip electrode 120 (e.g., disposed at the apex of the right ventricle of the heart 115), to the device 105. A second conductor of the multiconductor lead 110 can independently electrically couple a second electrode, such as a ring electrode 125, to the device 105. In an example, the device 105 can include a hermetically sealed housing 130, formed from a conductive metal, such as titanium. The housing 130 (also referred to as a "case" or "can") can be substantially covered over its entire surface by a suitable insulator, such as silicone rubber, except for at a window that forms a third electrode, referred to as a "case" or a "can" electrode 135. In an example, a header 140 can be mounted on the housing 130 such as for receiving the lead 110. The header 140 can be formed of an insulative material, such as molded plastic. The header 140 can also include at least one receptacle, such as for receiving the lead 110 and electrically coupling conductors of the lead 110 to the device 105. The header 140 can also include a fourth electrode, which can be referred to as an indifferent electrode 145.

FIG. 1 also illustrates generally portions of the device 105, together with schematic illustrations of connections to the various electrodes. The device 105 can include an electrical stimulation source, such as an exciter 150. The exciter 150 can delivers an electrical excitation signal, such as a strobed sequence of current pulses or other measurement stimuli, to the heart 115 (e.g., between the ring electrode 125 and the tip electrode 120, or using any other electrode configuration suitable for delivering the current pulses). The exciter 150 can be configured to receive one or more clock or other control signals from a controller 165. In response to the excitation signal provided by the exciter 150, a response signal can be sensed by signal processor 155 (e.g., between the tip electrode 120 and the indifferent electrode 145, or any other suitable electrode configuration). In an example, the response signal sensed by the signal processor 155 can be a voltage that represents a transthoracic (e.g., across a portion of the chest or thorax) impedance.

In an example, measuring tidal volume includes measuring an ohmic tidal volume using an impedance-derived ventilation signal. In an example, the impedance-derived ventilation signal, such as a minute ventilation signal, can be obtained by measuring transthoracic (across the chest or thorax) impedance. The measured transthoracic impedance can provide respiratory or ventilation information, including how fast and how deeply a patient is breathing. A component of transthoracic impedance varies as the patient inhales and exhales. Ventilation (e.g., breathing rate, which is also referred to as "ventilation rate" or "VR", and breathing volume, which is also referred to as "tidal volume" or "TV") information is included in the thoracic impedance signal. A ventilation representative impedance difference can be associated with an Ohmic TV. A minute ventilation signal (also referred to as "minute volume" or "MV") signal can be derived from the impedance signal, as illustrated by Equation (1a). MV measures airflow rate (e.g., liters per minute), Ohmic TV measures volume per breath (e.g., liters per breath), and VR measures breathing rate (e.g., breaths per minute).

$$MV = VR \times Ohmic\ TV \times k \quad (1a)$$

In equation (1a), "k" represents a conversion constant having the units of liters/ohm. A larger MV signal indicates a metabolic need for an increased heart rate, and a pacing rate can be adjusted accordingly by a cardiac rhythm management device, such as the device 105. We note that if the constant "k" is not available (which typically may be the case), then Equation (1b) applies, where an "ohmic minute ventilation" or "ohmic minute volume" having units ohms/minute can be related to the ventilation rate and ohmic tidal volume. Typically, as will be described later, this Ohmic MV can be used to adjust the heart rate.

$$Ohmic\ MV = VR \times Ohmic\ TV \quad (1b)$$

An example of an approach for measuring transthoracic impedance is described in Hauck et al., U.S. Pat. No. 5,318,597 entitled "RATE ADAPTIVE CARDIAC RHYTHM MANAGEMENT DEVICE CONTROL ALGORITHM USING TRANS-THORACIC VENTILATION," assigned to the assignee of the present application, the disclosure of which is incorporated herein by reference in its entirety, including its description of an approach for measuring and using transthoracic impedance.

In an example, the signal processor 155 can extract ventilation information, including the MV signal, from the impedance signal. Based at least in part on the MV signal, the signal processor 155 can output an indicated pacing rate signal at node 160 to the controller 165. Based on the indicated pacing rate signal at node 160, the controller 165 can adjust the rate of delivery of cardiac rhythm management therapy, such as electrical pacing stimuli, to the heart 115 by the therapy circuit 170. Such pacing stimuli can include, for example, providing bipolar pacing such as between the tip electrode 120 and the ring electrode 125, providing unipolar pacing such as between the can electrode 135 and either of the tip electrode 120 or the ring electrode 125, or providing pacing stimuli using any other suitable electrode configuration.

Figure 2:
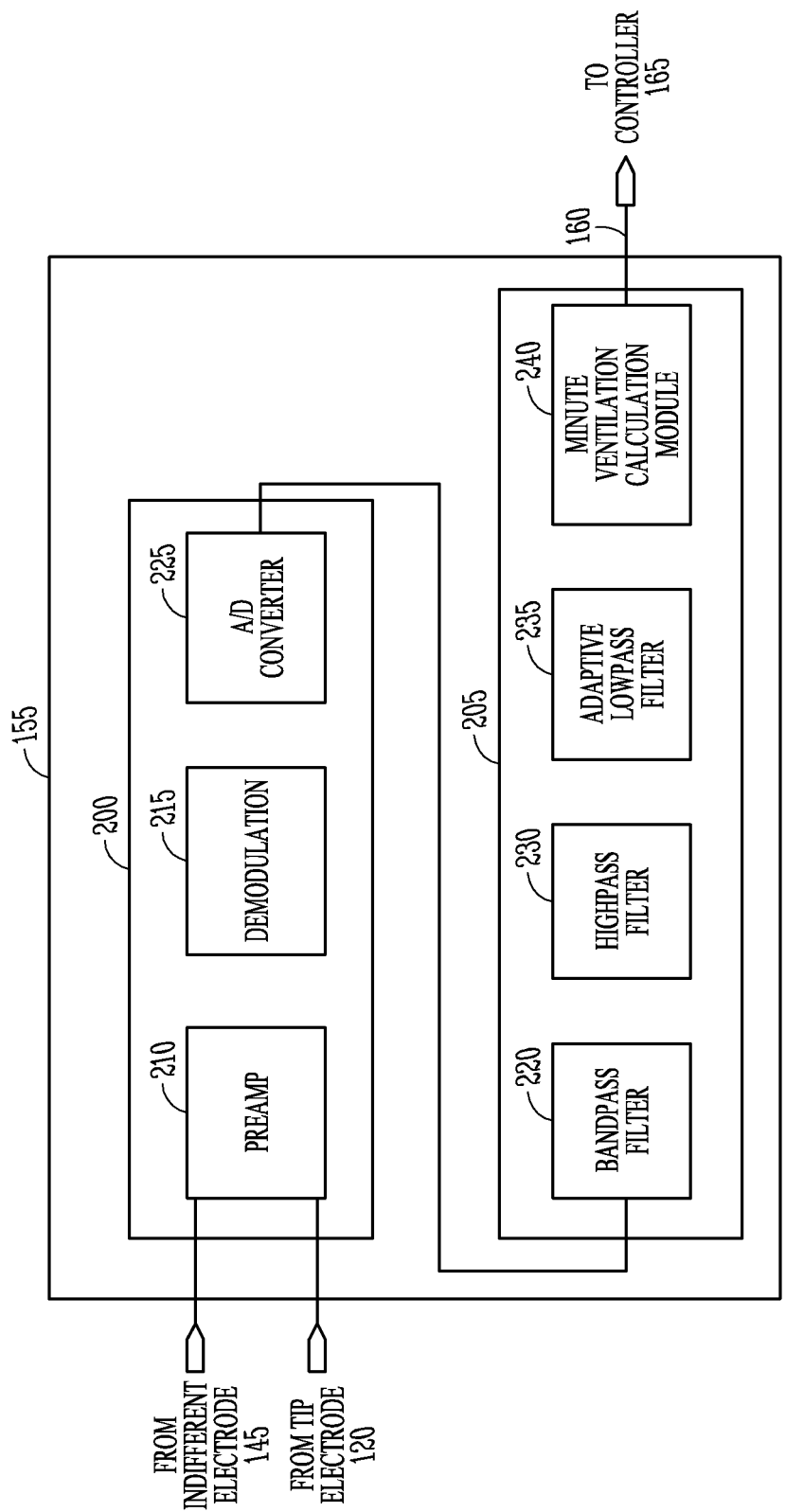
FIG. 2 is a block diagram illustrating generally an example of portions of a signal processor.

FIG. 2 illustrates generally an example of one or more portions of the signal processor 155. The signal processor 155 can include an analog signal processing circuit 200 and a digital signal processing circuit 205. Inputs of a preamplifier 210 (also referred to as a preamp or a receiver) of an analog signal processing circuit 200 can be electrically coupled to each of the indifferent electrode 145 and the tip electrode 120 such as for receiving a signal in response to the above-described stimuli provided by the exciter 150. The analog signal processing circuit 200 can also include a demodulator 215, such as receiving the output of the preamplifier 210, and providing an output signal to a bandpass filter 220. The output signal from the bandpass filter 220 can be received by an analog-to-digital (A/D) converter 225.

The A/D converter 225 can receive the output signal of the bandpass filter 220 and can provide a resulting digitized output signal to a high pass filter 230 of the digital signal processing circuit 205. In an example, the A/D converter 225 can be implemented as a 12-bit, successive approximation type switched-capacitor A/D converter having an input range of approximately 1 Volt. In one example, A/D converter 225 provides one 12-bit word corresponding to a sequence of current pulses delivered by exciter 150. Many different implementations of A/D converter 225 can be suitable for use in the present systems and methods. An output signal from A/D converter 225 can be received at the highpass filter 230 of the digital signal processing circuit 205.

In an example, the highpass filter 230 can include a single-pole infinite impulse response (IIR) digital filter that can receive a 12-bit digital output signal from the A/D converter 225. The highpass filter 230 can remove frequency components below its highpass cutoff frequency of approximately 0.1 Hz. Many other different examples of the highpass filter 230 may also be suitable for use in the present systems and methods. The highpass filter 230 can advantageously further attenuate baseline dc components of the transthoracic impedance, or low frequency shifts, such as may result from pulmonary edema or the like, and any dc-offset voltages created by A/D converter 225. In an example, the output of the highpass filter 230 can be provided to an adaptive lowpass filter 235 that attenuates frequency components of the signal that exceed the lowpass cutoff frequency of the adaptive lowpass filter 235. Attenuated frequencies can include the cardiac stroke signal, resulting from changes in blood volume in heart 115 as it contracts during each cardiac cycle, which appears as a component of the transthoracic impedance signal. In an example, the lowpass cutoff frequency of the filter 235 can be adaptively based on a heart rate of the patient. In an example, the lowpass cutoff frequency can be independent of any breathing rate signal obtained from the patient. In an example, the adaptive lowpass filter 235 can use a Chebyshev filter. In an example, the adaptive lowpass filter 235 can include an Elliptic filter. In an example, the adaptive lowpass filter 235 can use a state-space structure, rather than a conventional direct form structure. The state-space structure can further reduce the effects of coefficient quantization and round-off noise. An example of such a state-space structure is described in Leland B. Jackson, "Digital Filters and Signal Processing," $2^{nd}$ ed., pp. 332-340, Kluwer Academic Publishers, Boston, Mass., the disclosure of which is incorporated herein by reference.

In an example, a digital signal processing circuit 205 can be included within the controller 165 such as, for example, as a sequence of instructions executed by a microprocessor. In an example, the digital signal processing circuit 205 can include separately implemented hardware portions dedicated to performing the digital signal processing tasks described herein. An output signal from the highpass filter 230 can be received by the adaptive low pass filter 235 of the digital signal processing circuit 205. A minute ventilation (MV) calculation module 240 can receive an output signal from the adaptive lowpass filter 235, and can provide a resulting indicated pacing rate signal at node 160 to the controller 165.

In an example, an MV calculation module 240 can be implemented as a sequence of instructions executed on any suitable microprocessor. Alternatively, or in addition, the MV calculation module 240 can also be implemented as any other hardware or software configuration capable of calculating an indicated pacing rate based on ventilation information. An example of such a sequence of instructions executed on a microprocessor for calculating minute ventilation indicated rate is described below, and illustrated in FIG. 3.

The MV calculation module 240 can receive, from the adaptive low pass filter 235, a digital signal representing a time-varying transthoracic impedance. In an example, the impedance signal can be centered around zero, with positive values representing inhalation, and negative values representing exhalation. The maximum (most positive) and the minimum (most negative) values of the impedance signal can be stored in separate storage registers. After each breath, an interrupt can be provided to the microprocessor, such as upon each positive-going zero-crossing.

In an example, the signal processor 155 can be configured to determining a moving short-term average (STA) and a concurrent long-term average (LTA) of the ohmic minute ventilation. In an example, the STA can include carrying out an average of the ohmic minute ventilation over about 30 seconds. In an example, the LTA can include carrying out an average of the ohmic ventilation over about 4 hours to about 5 hours. The STA can represent the present minute ventilation indication of metabolic need. Similarly, the LTA can represent approximates the resting state of the patient. In an example, the LTA is carried out by an IIR digital filter. Other forms of central tendency or other measures of centrality can be obtained rather than averages or means.

In an example, the LTA and STA can be compared such as by subtracting one from the other. The difference can optionally be scaled, and can be used to adjust the pacing rate when the STA exceeds LTA. In an example, the pacing rate can be adjusted according to equation (2).

$$\text{SENSOR RATE DELTA}_{MV} = LRL + K_1(STA-LTA) \qquad (2)$$

In equation (2), "$K_1$" is a rate response factor that represents an optional scaling coefficient, LRL is a programmable lower limit to which the incremental sensor driven rate is added, and SENSOR RATE DELTA$_{MV}$ is the minute ventilation indicated rate at which pacing therapy is to be delivered. In an example, SENSOR RATE DELTA$_{MV}$ can be a linear function of the difference STA−LTA. Also, in this example, if the value of the short-term average (STA) is less than the value of the long-term average (LTA), then pacing therapy is delivered at the lower rate limit (LRL).

In an example, more than one scaling coefficient K can be used, such as for obtaining a piecewise linear mapping of minute ventilation to the resulting minute ventilation indicated rate. For example, when the STA−LTA difference exceeds a certain threshold value, a smaller scaling coefficient $K_1$ can be used. This reduces the incremental increase in pacing rate for high pacing rates, when compared to the incremental increase in pacing rate for pacing rates close to the lower rate limit (LRL).

In an example, a ratio STA/LTA may be used, rather than the difference STA−LTA used as described above. In such an example, the rate can be adjusted according to equation (3).

$$\text{SENSOR RATE DELTA}_{MV} = LRL + K_2(STA/LTA) \qquad (3)$$

In equation (3), STA represents the short-term average, LTA represents the long-term average, "$K_2$" is the rate response factor that represents an optional scaling coefficient, LRL is a programmable lower rate limit to which the incremental sensor driven rate is added, and SENSOR RATE DELTA$_{MV}$ is the minute ventilation indicated rate at which pacing therapy is delivered. If the value of the short-term average (STA) is less than the value of the long-term average (LTA), pacing therapy can be delivered at the lower rate limit (LRL). In an example, the LRL used can be about 60 beats per minute. In an example, a reduced incremental rate can be obtained for higher pacing rates by using more than one scaling coefficient, such as described above.

Other rate modifiers can also be used to obtain a minute ventilation indicated rate. Moreover, the minute ventilation indicated rate can be combined, blended, or otherwise used in conjunction with other rate indicators, such as those derived from different sensors providing different indicators of metabolic need (e.g., an acceleration sensor indicating a physical exertion level of a subject). Such indicators can have different response characteristics (e.g., time lag after onset of exercise) that can be advantageously combined with the minute ventilation rate indication described above. Moreover, although the above description has been represented in terms of rate between successive heart contractions, one of ordinary skill in the art would understand that this is for conceptual convenience, and that implementation may instead use the time interval between successive heart contractions, or an appropriate combination of heart rate and heart rate interval.

The present inventors have recognized, among other things, that obtaining the desired pacing rate response to MV can involve tailoring the MV rate response factor ($K_1$ or $K_2$), for the particular patient—which involves more effort for the physician or other user in programming the cardiac rhythm management device. For a particular patient, the measured TV can generally range from about 400 ml to about 4000 ml. The measured TV will generally depend upon the respiration rate (breathing rate) of the subject. Respiration rate generally varies within a range from about 6 breaths/minute to about 70 breaths/minute. In general, larger people having larger lungs generate larger thoracic impedance differences while breathing as opposed to the smaller thoracic impedance differences generated in people having smaller lungs. This is at least partially why the MV rate response factor must generally be tailored for the particular patient.

However, the present inventors have also recognized that can be possible to automatically tailor the MV rate response factor for the particular patient, such as based on a TV measurement of the particular patient, and on population-derived information from other patients.

Figure 3:
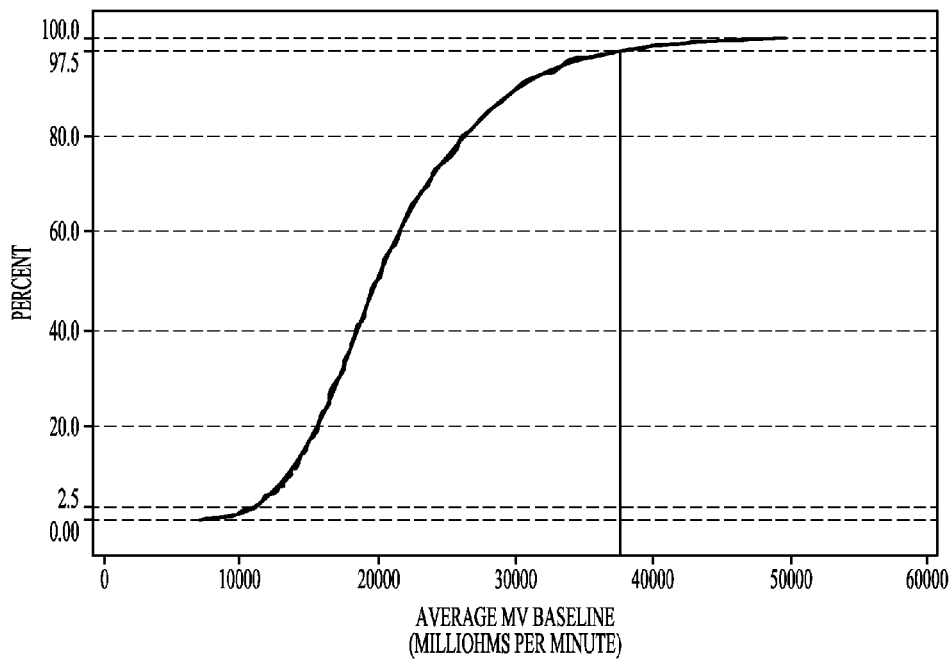
FIG. 3 is a graph showing a cumulative distribution function of the long-term average of MV for a population.

FIG. 3 illustrates a curve showing a cumulative distribution function of a long-term average of MV for a patient population, such as was obtained from a sample of a large number of patients. In the example of FIG. 3, the average MV ranges from a lower limit of about 10,000 milliohms per minute to an upper limit of about 40,000 milliohms per minute for about 95% of the sampled patient population. In the example of FIG. 3, the ratio of the upper limit of MV to the lower limit of MV for resting breathing can be determined to be about 4:1. The present inventors have recognized that this ratio can be used to determine a normalization factor that can be used to normalize an ohmic tidal volume measured for a particular patient, such as by using FIG. 4.

Figure 4:
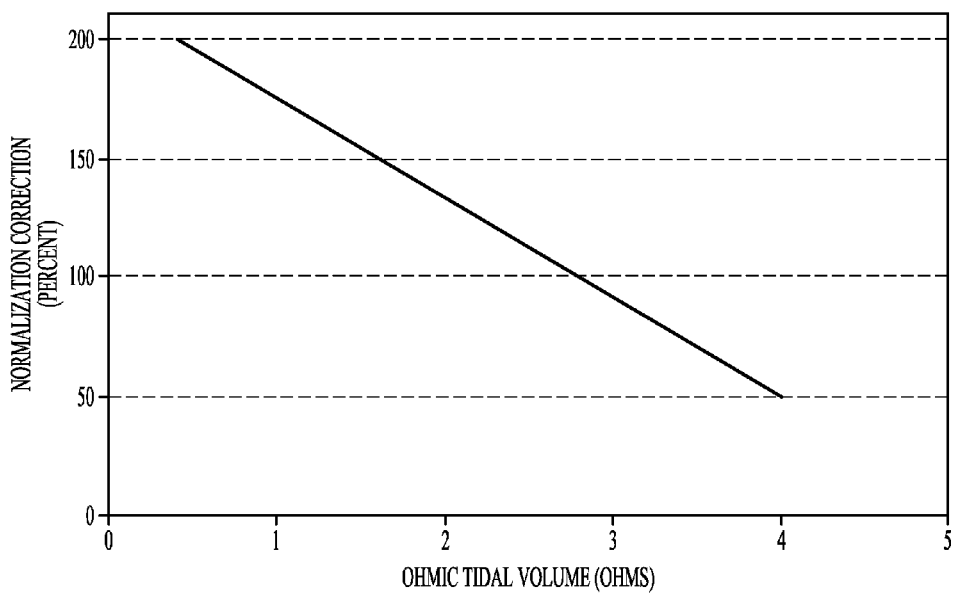
FIG. 4 is a graph showing an inverse relationship between normalization correction percentage and ohmic tidal volume.

FIG. 4 is a graph illustrating a normalization factor vs. ohmic tidal volume. The x-axis of the graph represents ohmic tidal volume in ohms and the y-axis represents a normalization factor, shown as a percentage value. In this example, the normalization factor range extends over the same 4:1 range as indicated in FIG. 3, which can be mapped (e.g., inversely linearly) to the range of ohmic tidal volumes expected to be measured for a particular patient (e.g., from about 400 milliohm to about 4000 milliohm). The relationship shown in FIG. 3 can be used to select a particular normalization factor for a particular patient using a measurement of ohmic tidal volume from that patient. The selected normalization factor can be used to adjust the MV rate response factor, K, described above. This can allow a single MV rate response factor, K, to be programmed into the cardiac rhythm management device for all patients, if desired—the device can automatically adjust K using the normalization factor selected using FIG. 4 (which is based on the measured ohmic tidal volume of the patient), so that the resulting effective MV rate response factor is automatically appropriately tailored for the particular patient.

Figure 5:
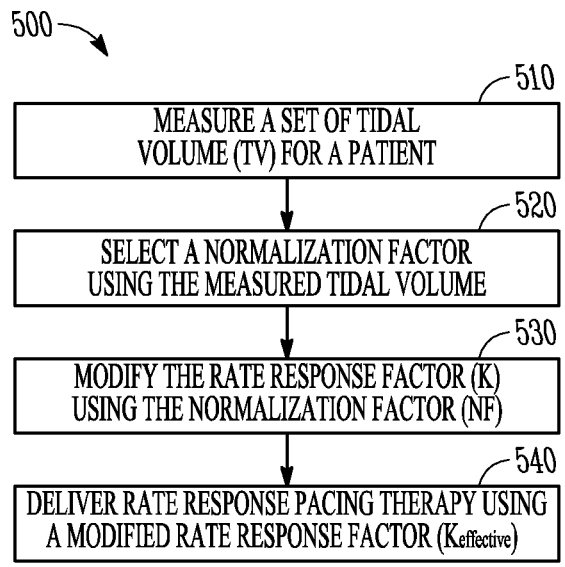
FIG. 5 is a diagram illustrating generally an example including adjusting a rate response factor (K) for a minute ventilation or similar ventilation sensor in a cardiac rhythm management system.

FIG. 5 is a chart illustrating generally an example 500 including automatically tailoring a rate response factor for a particular patient.

At 510, resting TV can be measured for the particular patient, such as by using a single TV measurement or a central tendency (e.g., average, median, etc.) of a plurality of TV measurements (e.g., such as over a period that can range from about 2 minutes to several hours). In an example, while the average tidal volume is measured over a short time period (e.g. 2 minutes), a "quick calibration" is performed by having the patient sit quietly and breathe normally without talking. A much longer calibration period (e.g., 6 hours) can be used to perform an "automatic" calibration. During the automatic calibration, the patient may carry on normal activities, wherein it is presumed that a large portion of the time period will be spent in a resting state so that the average tidal volume thus obtained will reflect the resting tidal volume.

At 520, a normalization factor (NF) can be selected, such as by using the TV measured for the particular patient as an x-axis index for selecting a corresponding NF, such as by using the graph of FIG. 4 to obtain the corresponding y-axis value for use as the NF. For example, NF can be calculated such as by using equation (4).

$$\text{Normalization Factor (NF)} = (Y\text{intercept}) + (\text{Slope}) * (TV_{Avg}) \quad (4)$$

At 530, the MV rate response factor, K, can be adjusting using the normalization factor, such as by multiplying K by NF to obtain an effective MV rate response factor $K_{effective}$, which has been automatically tailored to be appropriate for the particular patient. This can be expressed as shown in equation (5).

$$\text{Effective Rate Response Factor } (K_{Effective}) = NF * K \quad (5)$$

At 540, rate responsive pacing or cardiac resynchronization therapy can be delivered to the particular patient, such as by using $K_{effective}$ in place of K in Equation (2) or Equation (3), above.

Figure 6:
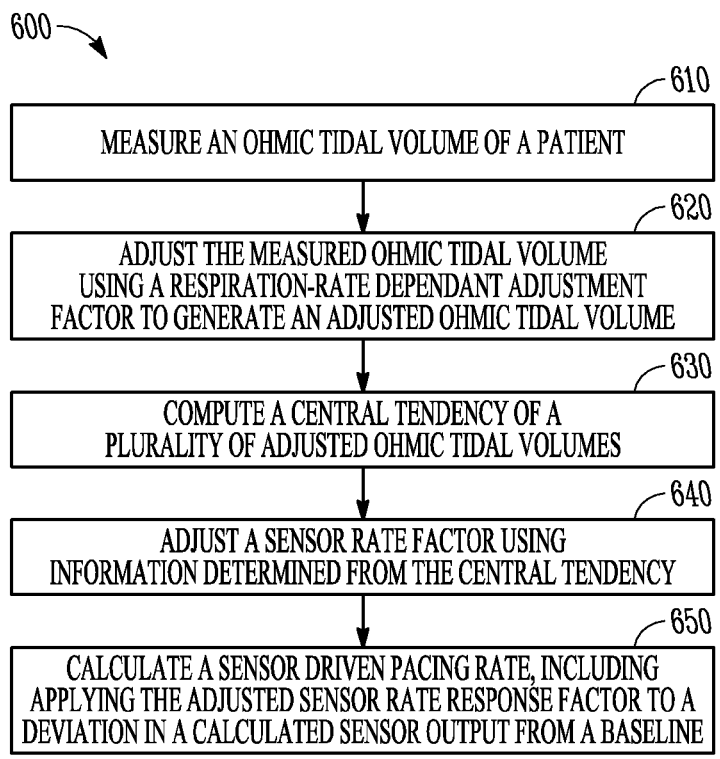
FIG. 6 is a diagram illustrating generally an example including adjusting a rate response factor (K) for a minute ventilation or similar ventilation sensor in a cardiac rhythm management system, including adjusting the measured tidal volume by a respiration-rate dependent factor, such as to adjust for a filter non-ideality.

FIG. 6 illustrates generally an example 600 including adjusting the rate response of a ventilation sensor. The present inventors have recognized, among other things, that in certain instances, the TV measurement can be obtained using a CRM device in which the TV measurement may exhibit a slight dependence on breathing rate, such as due to a frequency dependence in one or more of the bandpass filter 220, the highpass filter 230, or the adaptive lowpass filter 235 of FIG. 2. In such a case, it may be desirable to correct the TV measurement for such frequency dependence before using it in FIG. 4 as the x-axis index for obtaining the y-axis normalization factor, NF. Such correction of the TV measurement can involve measuring the breathing rate (respiration rate), and applying an inverse function of the non-ideality in the filtering to obtain a corrected TV measurement, for use with FIG. 4 in selecting the NF. An example of using this TV measurement is described with respect to the example 600 of FIG. 6.

At 610, an ohmic tidal volume (TV) of a patient can be measured. This can include taking a difference between maximum and minimum values of a thoracic impedance signal, held in corresponding storage registers, for the patient's previous breath. A larger tidal volume indicates a deeper breath than a smaller tidal volume. A tidal volume measurement can be generated at 610 for individual breaths taken by the patient.

At 620, the measured ohmic tidal volume can be adjusted using a respiration-rate dependent adjustment factor to generate an adjusted ohmic tidal volume. For example, the respiration-rate dependent adjustment factor can be generated by applying an inverse function to that of the non-ideality in any non-ideal filters used in the signal processing circuit 205, such as to compensate for any non-idealities.

At 630, a central tendency of the adjusted ohmic tidal volumes can be computed, and used with FIG. 4 as the x-axis index for obtaining the y-axis normalization factor, NF.

At 640, a minute ventilation sensor rate response factor, K, can be adjusted to obtain a $K_{effective}$. This adjustment can involve using the normalization factor, NF, that was obtained using information determined from the central tendency computed at 630.

At 650, a minute ventilation sensor driven pacing rate can be calculated, including applying the adjusted minute ventilation sensor rate response factor to a deviation in a calculated minute ventilation sensor output from a baseline.

Figure 7:
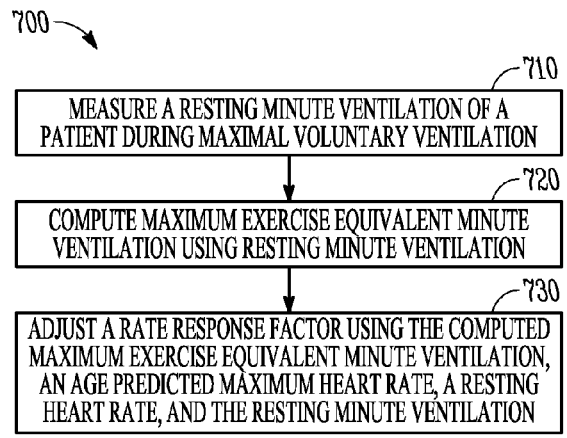
FIG. 7 is a diagram illustrating generally an example including determining a minute ventilation rate-response factor correction using one or more factors, and optionally usable in conjunction with the techniques described with respect to FIG. 5 or FIG. 6.

FIG. 7 represents another technique of adjusting the rate response factor, for example, in the case of individuals who are not representative of the population shown in FIG. 3 or in cases where the physician believes the technique of FIG. 7 may be better suited for the individual (e.g., if they have lung disease or are very athletic). In an example, this technique can be used along with or independently of the population base normalization examples discussed above. FIG. 7 illustrates generally an example 700 for adjusting the rate response of the minute ventilation sensor. The present inventors have recognized, among other things, that measuring maximum voluntary ventilation (MVV) in a patient can allow a cardiac rhythm management (CRM) device to predict a sensor rate response factor. MVV represents the greatest volume of gas that can be breathed per minute by voluntary effort, and can be measured by requesting that a patient forcibly breath as deeply and rapidly as possible.

In most individuals, the minute ventilation during exercise does not meet the pulmonary mechanical limit of MVV but is generally about 25% lower. In terms of the population the peak minute ventilation observed during maximal exercise can range from 0.61 to 1.07 of MVV. The lower limit is reached by individuals with chronic pulmonary obstructive disease (COPD) while the other extreme (1.07) is reached by well trained athletes.

A cardiovascular limitation can be distinguished from a pulmonary limitation, in an example, by comparing an individual's peak exercise ventilation and the individual's resting MVV measurement. The patient's ventilatory reserve can be estimated by knowing the disease status (e.g., COPD, etc.) of the patient and the patient's resting MVV. If desired, the signal processing circuit 205 can be configured to provide an MV rate response that can substantially match the patient's ventilatory reserve to the patient's heart rate reserve.

At 710, a resting MV of a patient can be measured during a maximal voluntary ventilation (MVV), such as by requesting the patient to forcibly breath as deeply and rapidly as possible for a prescribed time (e.g., 12 to 15 seconds) under a physician's supervision. The external programmer 190 can be used to activate MV measurement before the MVV forcible breathing maneuver. The signal processing circuit 205 can calculate the resting minute ventilation by measuring the transthoracic impedance during the MVV maneuver. The external programmer 190 can generate an audible or visual indication indicating that the calibration has been completed, so that the patient can discontinue the MVV forcible breathing maneuver.

At 720, a maximum exercise equivalent minute ventilation can be computed, such as by using the resting minute ventilation measured at 710. The maximum exercise equivalent minute ventilation can be computed using equation (6).

$$\text{Max Exercise Equivalent } MV = MVV \times \text{Scaling Factor} \quad (6)$$

The minute ventilation observed during the MVV forcible breathing maneuver is multiplied by a scaling factor (e.g., 0.75). In an example, the scaling factor can be any specified value within the range including from about 0.67 to about 1.07. In an example, the nominal scaling factor that can be used is about 0.8. A scaling factor below the lower limit (e.g., below 0.67) can be used for COPD patients.

At 730, a minute ventilation sensor rate response factor can be adjusted using the computed maximum exercise equivalent minute ventilation, an age predicted maximum heart rate, a resting heart rate, and the resting minute ventilation. The age predicted maximum heart rate (HR) can be given by equation (7):

$$HR = 220 - (\text{Age of the patient}) \quad (7)$$

Figure 8:
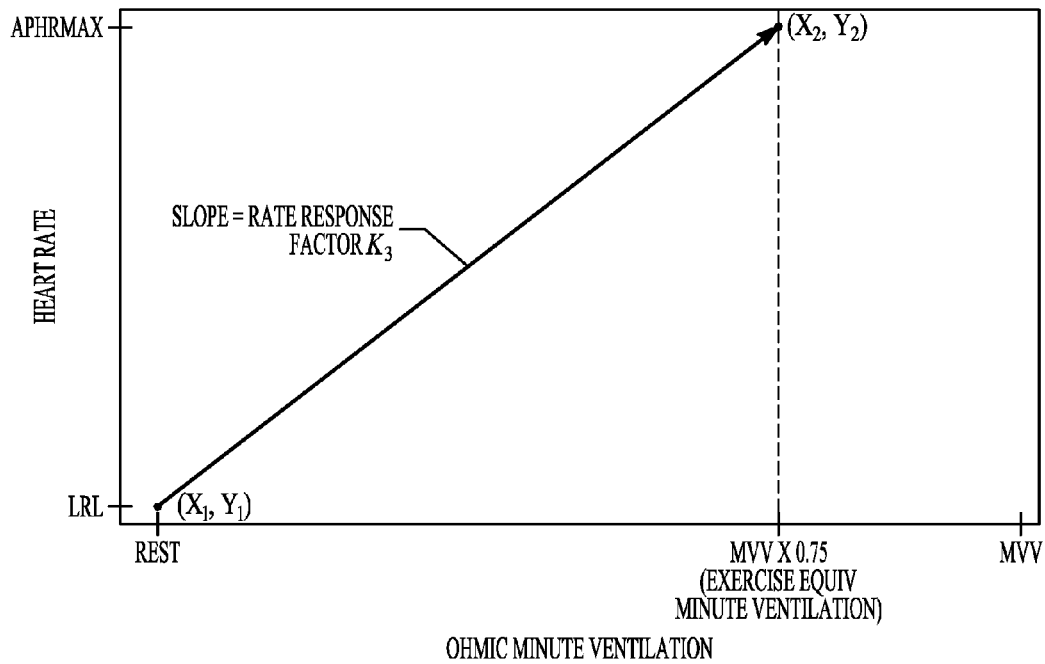
FIG. 8 is a graph showing a relationship between heart rate and minute ventilation.

For example, based on the equation (7), a 50-year-old patient can be predicted to have an age-predicted maximum heart rate of 170. In an example illustrated in FIG. 8, after MV calibration at 710 and computing the maximum exercise equivalent minute ventilation at 720 (Eq. 6), two points (x1, y1) and (x2, y2) can be plotted on the graph. The heart rate is shown on the y-axis and ohmic minute ventilation on the x-axis. The first point includes an x-coordinate (x1) that corresponds to the minute ventilation at rest (i.e. after calibration, labeled REST in the graph) and a y-coordinate (y1) that corresponds to the Resting Heart Rate (which in a pacemaker patient is the Lower Rate Limit—LRL). The second point (x2, y2) includes an x-coordinate (x2) that corresponds to the maximum exercise equivalent minute ventilation and a y-coordinate (y2) that corresponds to the age predicted maximum heart rate (e.g. APHRMAX=220−patient age). The line drawn between (x1, y1) and (x2, y2) is the MV rate response factor, $K_3$.

The MV rate response factor $K_3$ determined in this fashion will be equivalent in most cases to the earlier $K_{effective}$ which was derived from population data and which occurs automatically as part of calibration. The MVV derived K3 may be determined prior to the population derived $K_{effective}$ is calculated. In either case it will supplant the population derived $K_{effective}$ until the next MV calibration of the device. (Note: the MV calibration is good for the life of the device unless there is a lead revision or the user requests another calibration.)

The above description illustrates, by way of example, but not by way of limitation, a particular example of the present devices and methods in which ventilation information can be extracted from a detected transthoracic impedance, and the rate of delivery of cardiac rhythm management therapy can be adjusted based on an indicator derived from the ventilation information. However, the present devices and methods can also include extraction of other information (e.g., cardiac stroke information) from the transthoracic impedance, such as for adjusting the rate of delivery of cardiac rhythm management therapy based on an indicator extracted from such information. One such example is disclosed in Spinelli U.S. Pat. No. 5,235,976 entitled, "METHOD AND APPARATUS FOR MANAGING AND MONITORING CARDIAC RHYTHM MANAGEMENT USING ACTIVE TIME AS THE CONTROLLING PARAMETER," which is assigned to the assignee of the present patent application, and the disclosure of which is incorporated herein by reference.

Additional Notes

An implantable medical device (IMD) may include one or more of the features, structures, methods, or combinations thereof described herein. For example, a cardiac monitor or a cardiac stimulator can be implemented to include one or more of the advantageous features or processes described above. It is intended that such a monitor, stimulator, or other implantable or partially implantable device need not include all of the features described herein, but can be implemented to include selected features that provide for unique structures or functionality. Such a device can be implemented to provide a variety of therapeutic or diagnostic functions.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A cardiac rhythm management system comprising:
a signal processor configured to:
measure a tidal volume of a patient;
adjust the measured tidal volume using a ventilation rate dependent adjustment factor to generate a ventilation rate compensated tidal volume, wherein the ventilation rate dependent adjustment factor is configured to compensate for a filter non-ideality in the signal processor, and
adjust a ventilation sensor rate response factor using information determined from the ventilation rate compensated tidal volume; and
a controller, coupled to the signal processor, the controller configured to calculate a ventilation sensor driven pacing rate, including applying the adjusted ventilation sensor rate response factor to a deviation in an observed ventilation sensor output from a baseline.

2. The system of claim 1, wherein the signal processor is configured to adjust the ventilation sensor rate response factor using information obtained from a patient population.

3. The system of claim 1, wherein the signal processor includes or is coupled to a memory configured to store a plurality of resting tidal volumes, and wherein the signal processor comprises a central tendency computation circuit configured to compute a central tendency of the plurality of resting tidal volumes.

4. The system of claim 1, wherein the signal processor is configured to adjust the ventilation sensor rate response factor using information determined from the ventilation rate compensated tidal volume, including using the ventilation rate compensated tidal volume to determine a normalization factor using a population-determined relationship between the tidal volume and the normalization factor.

5. The system of claim 4, wherein the population-determined relationship between the ventilation rate compensated tidal volume and the normalization factor is a substantially inverse linear relationship for the normalization factor as a function of the ventilation rate compensated tidal volume.

6. The system of claim 4, wherein the population-determined relationship between the ventilation rate compensated tidal volume and the normalization factor represents about a 4-to-1 range of the normalization factor over an expected range of tidal volumes for the population.

7. The system of claim 1, wherein the signal processor is configured to adjust a ventilation sensor rate response factor using information determined from the ventilation rate compensated tidal volume, comprising:
using a population-based ventilation rate response factor programmed into a cardiac rhythm management device; and
automatically adjusting the population based ventilation rate response factor for the patient using a normalization factor determined using the ventilation rate compensated tidal volume of the patient.

8. The system of claim 1, wherein the signal processor is configured to adjust a ventilation sensor rate response factor using a measured minute ventilation at rest, an exercise equivalent minute ventilation, a resting heart rate, and an age predicted maximum heart rate determined for the patient.

* * * * *